US008329922B2

(12) United States Patent
Zhou et al.

(10) Patent No.: US 8,329,922 B2
(45) Date of Patent: Dec. 11, 2012

(54) CRYSTALLINE SODIUM ATORVASTATIN

(75) Inventors: Kailan Zhou, Jiaojiang (CN); Hong Liu, Jiaojiang District of Taizhou (CN); Zhirong Chen, Jiaojiang District of Taizhou (CN); Huabin Hong, Jiaojiang District of Taizhou (CN); Yang Sun, Jiaojiang District of Taizhou (CN); Yunde Wang, Jiaojiang District of Taizhou (CN); Jiangchun Pan, Jiaojiang District of Taizhou (CN)

(73) Assignee: Arrow International Limited, Valetta, MT (US)

(*) Notice: Subject to any disclaimer, the term of this patent is extended or adjusted under 35 U.S.C. 154(b) by 21 days.

(21) Appl. No.: 13/324,678

(22) Filed: Dec. 13, 2011

(65) Prior Publication Data

US 2012/0095072 A1 Apr. 19, 2012

Related U.S. Application Data

(63) Continuation of application No. 11/504,104, filed on Aug. 15, 2006, now Pat. No. 8,097,734.

(30) Foreign Application Priority Data

Aug. 15, 2005 (CN) .......................... 2005 1 0060395
Jul. 7, 2006 (GB) .................................. 0613566.9

(51) Int. Cl.
*C07D 405/04* (2006.01)
*A61K 31/40* (2006.01)

(52) U.S. Cl. ....................................... 548/537; 514/423

(58) Field of Classification Search .................. 548/537; 514/423

See application file for complete search history.

(56) References Cited

U.S. PATENT DOCUMENTS

| | | | |
|---|---|---|---|
| 4,681,893 | A | 7/1987 | Roth |
| 5,273,995 | A | 12/1993 | Roth |
| 5,686,104 | A | 11/1997 | Mills et al. |
| 7,411,075 | B1 | 8/2008 | Ayalon et al. |
| 2007/0066678 | A1 | 3/2007 | Zhou et al. |

FOREIGN PATENT DOCUMENTS

| | | |
|---|---|---|
| CN | 1749247 | 3/2006 |
| CN | 1749248 | 3/2006 |
| EP | 0409281 | 1/1991 |
| EP | 1535613 | 6/2005 |
| EP | 1577297 | 9/2005 |
| GB | 2424880 | 10/2006 |
| WO | 97/03959 | 2/1997 |
| WO | 01/36384 | 5/2001 |
| WO | 03/068739 | 8/2003 |
| WO | 2005/073187 | 8/2005 |
| WO | 2005/090301 | 9/2005 |
| WO | 2005/092852 | 10/2005 |
| WO | 2005/105738 | 11/2005 |
| WO | 2006/021969 | 3/2006 |
| WO | 2006/032959 | 3/2006 |

OTHER PUBLICATIONS

A. Schuemacher, International Search Report and Written Opinion of the International Search Authority for International Application No. PCT/GB2006/003035, Nov. 22, 2006, European Patent Office, Rijswijk, Netherlands.

A. Schuemacher, International Preliminary Report on Patentability for International Application No. PCT/GB2006/003035, Nov. 2, 2007, European Patent Office, Munich, Germany.

A. Schuemacher, International Preliminary Report on Patentability for International Application No. PCT/GB2006/003025, Nov. 2, 2007, European Patent Office, Munich, Germany.

S.R. Byrn et al., Solid State Chemistry of Drugs, Chapter 11, Hydrates and Solvates, pp. 233-247, 2d. ed. (1999).

A.M. Rouhi, The Right Stuff, Chemical & Engineering News, vol. 81, No. 8, pp. 32-35 (2003).

H.G. Brittain (ed.), Polymorphism in Pharmaceutical Solids, vol. 95, pp. 1-219 (1999).

S.L. Morisette et al., High-throughput crystallization: polymorphs, salts, co-crystals and solvates of pharmaceutical solids, Advanced Drug Delivery Reviews 56, pp. 275-300 (2004).

S. Byrn et al., Pharmaceutical Solids: a Strategic Approach to Regulatory Considerations, Pharm. Res., vol. 12, No. 7, pp. 945-954 (1995).

P.W.K. Woo et al., Atorvastatin, an HMG-CoA Reductase Inhibitor and Efficient Lipid-Regulating Agent. Part I. Sythesis of Ring-Labeled [14C]Atorvastatin, J. Labelled Cpd. Radiopharm. 42:121-127 (1999).

P.W.K. Woo et al., Atorvastatin, an HMG-CoA Reductase Inhibitor and Efficient Lipid-Regulating Agent. Part III. Sythesis of [2H5]-, [13C8], and [13C7,15N] Atorvastatin and their Application in Metabolic and Pharmacokinetic Studies, J. Labelled Cpd. Radiopharm. 42:135-145 (1999).

D.L. Sparks et al., Hmg-CoA Reductase Inhibitors (Statins) in the Treatment of Alzheimer's disease and Why it Would be Ill-Advised to Use on that Crosses the Blood-Brain Barrier, J. Nutr. Health Aging 6:324-331, Serdi Publisher (2002) (Abstract, Accession No. NLM12474023).

A. Schuemacher, International Search Report for International Application No. PCT/GB2006/003025, Nov. 22, 2006, European Patent Office, Netherlands.

Office Action mailed Mar. 3, 2009 in U.S. Appl. No. 11/504,103 to Zhou, K. et al.

Amendment and Reply Under 37 C.F.R. § 1.111 filed May 28, 2009 in U.S. Appl. No. 11/504,103, to Zhou, K. et al.

Office Action mailed Nov. 25, 2009 in U.S. Appl. No. 11/504,103 to Zhou, K. et al.

Lambert et al., Organic Structural Spectroscopy (1998), p. 202, Upper Saddle River, NJ.

Bernstein, Polymorphism in Molecular Crystals (2002), pp. 1-10 and 240-242.

*Primary Examiner* — Robert Havlin
(74) *Attorney, Agent, or Firm* — Florek & Endres PLLC

(57) ABSTRACT

Crystalline sodium atorvastatin, compositions containing the same and methods for the production thereof.

22 Claims, 2 Drawing Sheets

CRYSTALLINE SODIUM ATORVASTATIN

Figure 1:
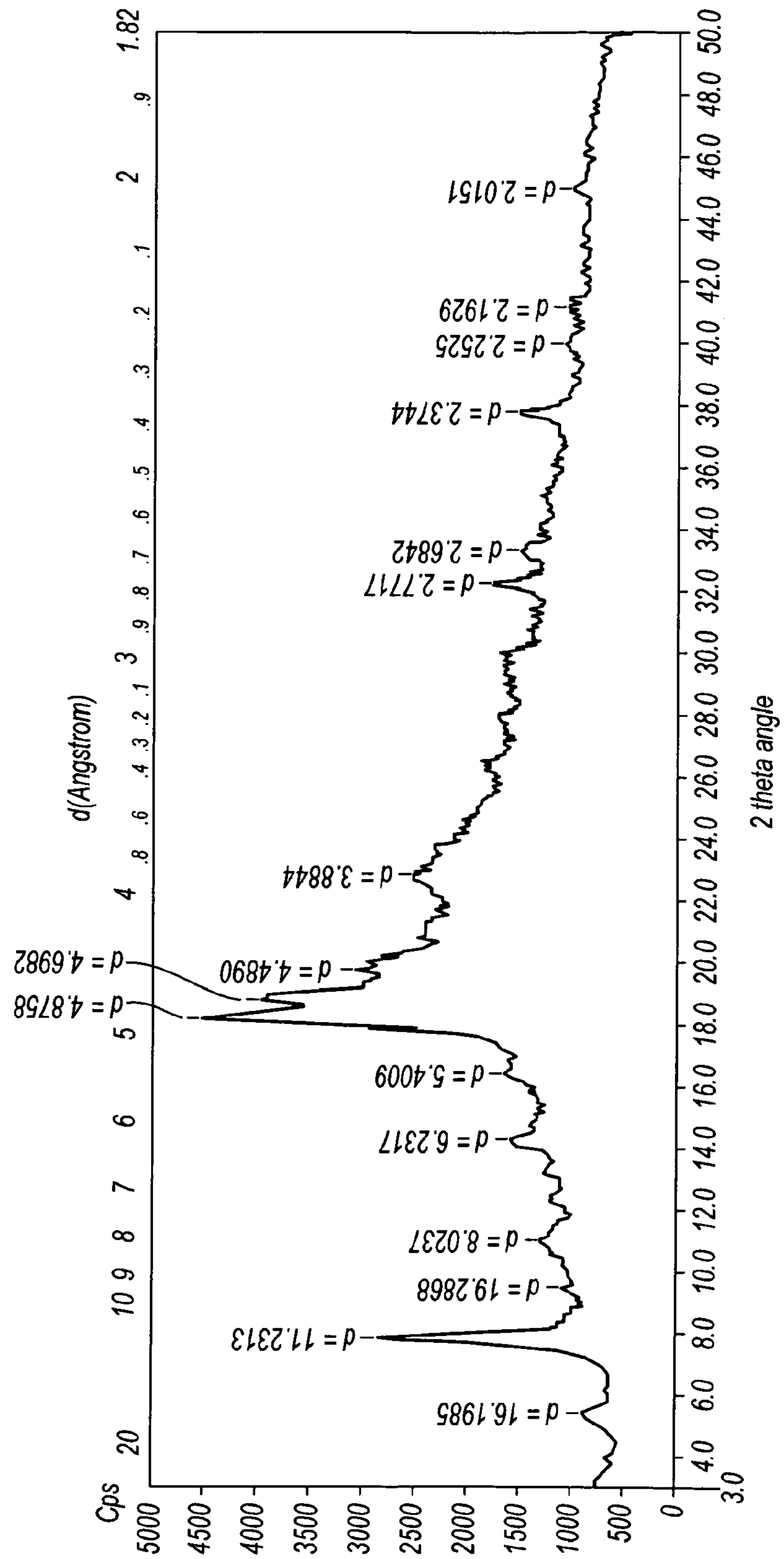

The present application is a continuation of U.S. Ser. No. 11/504,104, filed Aug. 15, 2006, now allowed.

The present invention relates to crystalline sodium atorvastatin, to compositions containing the same and to methods for the formation thereof.

Cerebrovascular disease is often considered to be one of the biggest threats to human health. According to one investigation, there are more than three million people who die of the disease annually in China, the disease being responsible for 50% of all deaths. 75% of survivors lose their working abilities in different degrees and 4% are badly affected. Moreover, 80% of adults aged thirty or above may have cerebrovascular disease in one of its forms, such as hyperlipemia, hypertension, coronary heart disease (CHD), and cerebral apoplexy.

Atherosclerosis is the pathological basis of ischemic cerebrovascular disease (ICVD). Death rates due to central brain related coronary heart disease and cerebrovascular disease have recently increased and, therefore, research into treatments for atherosclerosis is becoming more and more important.

Atherosclerosis is the aggradation of blood ingredients, hyperplasia of smooth muscle cells and of collagenous fibre in the artery endothelium. The lesions, which result from an excessive, inflammatory-fibroproliferative response to various forms of injury to the endothelium and smooth muscle of the artery wall, affect large elastic arteries, such as the main artery and its first branch, and medium muscle arteries, such as cerebral arteries, coronary arteries, renal arteries and arterial branches of arteries at the extremities. Lesions are commonly found at the openings of vas endothelium branches which are easily damaged. The lesions are plaque-distributed and force the vas to be harder, narrow or block the chamber and then result in absence of blood in the tissues and organs. Hence, the most likely effect is myocardial infarction and cerebral infarction. The cause of atherosclerosis is not fully understood because of the many complex factors involved in this disease. In general, there are two main types of factors, the first being constitutional factors such as age, sex and familial inheriting factors, and the second being acquired factors, such as hyperlipemia, hypertension, over-smoking, diabetes and over-adiposity. All of these will affect and increase the atherosclerosis owing to their collective multi-factorial actions.

There are several kinds of anti-atherosclerosis drugs, such as lipid regulating agents, anti-oxidants, diluents of fatty acids and protectors of arterial endothelium. The HMG-CoA Reductase Inhibitors are lipid regulating agents and include drugs of the statin family, such as mevastatin, lovastatin, simvastatin, fluvastatin and atorvastatin, which are considered to be the best cholesterol lowering statin medicines available. All are the first choice for treating diseases such as primary hyperlipemia, heterozygote familial hiperlipemia, high lipoprotein (III), diabetes and renal hyperlipemia. There are a large number of scientists researching these kinds of medicines and they have already reported a number of technical methods. For example, the ability to obtain a high purity of HMG-CoA Reductase Inhibitor, as disclosed in Chinese patent application 9981076.0, relies on "displacement of color spectrum" to separate the HMG-CoA Reductase Inhibitor.

Although this method results in a high purity of HMG-CoA Reductase Inhibitor with a high yield, a low cost and minimal effect on the ecological balance, it applies the "displacement of color spectrum" technique at the same time as utilising a chromatographic column. The principle is traditional laminar analysis, which always takes a long time to perform and requires the skills of a professional researcher to operate it. In addition, it is difficult to perform in large-scale automated production.

Accordingly, this method is used to purify small quantities of HMG-CoA Reductase Inhibitor at a laboratory scale only. It is not used for purifying atorvastatin because of the difficulty in regenerating the chromatographic column. Atorvastatin, which is a new generation of the statin family antihyperlipemias, is used, among other things, for common hyperlipemia or mixed hyperlipidemia, which result mainly from increased blood cholesterol. It is especially useful for patients who are unresponsive to other medicines.

It is thought that some of the statin family medicines have good efficacy when they are used with other antihyperlipemia drugs, however, atorvastatin has been shown to have sufficient efficacy when administered alone. Hence, the sales of atorvastatin are increasing dramatically such that it is now the best selling statin family medicine on the market.

Chinese patent application number 02815070.8 discloses methods for the production of crystalline calcium atorvastatin. It discloses two crystalline forms, VI and VII of [R-(R<*>, R<*>)]-2-(4-Fluorophenyl)-beta, delta-dihydroxy-5-(1-methylethyl)-3-phenyl-4-[phenylamino)carbonyl]-1H-pyrrole-1-heptanoic acid calcium salt. According to the methods, nine steps are needed to isolate Form VI and five steps to isolate Form VII. The crystalline calcium atorvastatin produced is more than 99.0% pure by HPLC, however, due to the complex purifying process, the methods used are very expensive. The methods also require the use of nitrile as a purifying agent which is not only harmful to the environment, but also to the workers involved.

It is, therefore, an object of the present invention to seek to alleviate these problems.

A further object of the present invention is to provide crystalline sodium atorvastatin in various polymorphic forms and processes for the preparation thereof.

According to a first aspect of the present invention, there is provided crystalline sodium atorvastatin.

According to a further aspect of the present invention, there is provided crystalline sodium atorvastatin which exhibits an X-ray diffraction pattern comprising peaks expressed in degrees two-theta at approximately 3.36±0.2, 8.3±0.2, 8.81±0.2, 9.69±0.2, 19.48±0.2, 20.86±0.2 and 22.88±0.2.

According to another aspect of the present invention, there is provided crystalline sodium atorvastatin which exhibits an X-ray diffraction pattern comprising peaks expressed in degrees two-theta at approximately 3.36±0.2, 4.8±0.2, 5.59±0.2, 7.41±0.2, 8.3±0.2, 8.81±0.2, 9.69±0.2, 10.24±0.2, 11.13±0.2, 11.21±0.2, 12.22±0.2, 12.8±0.2, 13.85±0.2, 15.99±0.2, 16.40±0.2, 16.95±0.2, 17.82±0.2, 18.15±0.2, 18.46±0.2, 19.48±0.2, 20.86±0.2, 21.82±0.2, 22.88±0.2, 23.98±0.2, 28.34±0.2, 32.27±0.2 and 33.40±0.2.

Figure 2:
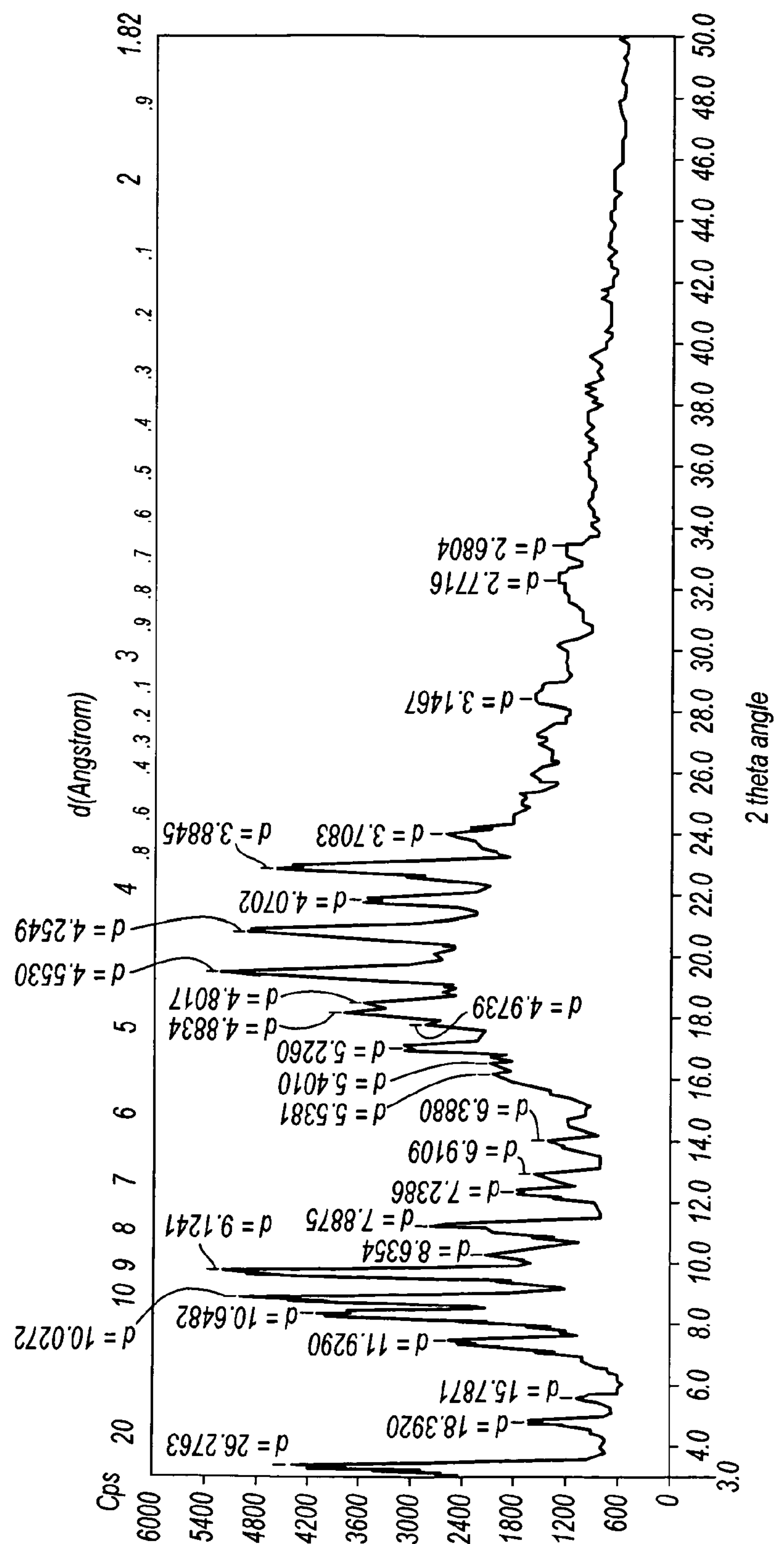

Also provided by the present invention is crystalline sodium atorvastatin which exhibits an X-ray diffraction pattern substantially the same as shown in FIG. 2.

According to further aspect of the present invention, there is provided a method for the preparation of crystalline sodium atorvastatin, the method comprising:—

(a) adding amorphous sodium atorvastatin to a first organic solvent to form a first solution;

(b) adding a second organic solvent to the first solution to form a second solution;

(c) allowing sodium atorvastatin to crystallize out from the solution; and (d) collecting the crystallized sodium atorvastatin.

Preferably, the first organic solvent is an alcohol, more preferably a straight or branched $C_1$ to $C_6$ alcohol, further preferably ethanol.

In preferred embodiments, the second organic solvent is a ketone, more preferably acetone.

Preferably, the amorphous sodium atorvastatin is added to the first organic solvent at a ratio of about 8 to 10 g amorphous atorvastatin for about every 40 g to 100 g first organic solvent.

Preferably, the second organic solvent is added to the first solution at a ratio of about 50 to 100 g second organic solvent for about every 8 to 10 g amorphous atorvastatin used in step (a).

The first organic solvent preferably comprises at least about 75% organic solvent in solution. Preferably, the crystallized sodium atorvastatin is collected by filtration. It is preferred that the collected crystallized sodium atorvastatin is dried, more preferably dried under vacuum.

In further embodiments of the present invention, the method comprises the following additional steps for the preparation of amorphous sodium atorvastatin for use in step (a):—

(i) preparing a third solution comprising sodium atorvastatin;
(ii) adjusting the pH of the third solution to an acid pH;
(iii) adding a third organic solvent to form a fourth solution;
(iv) isolating an organic layer;
(v) adjusting the pH of the organic layer to an alkali pH;
(vi) collecting precipitated amorphous sodium atorvastatin.

Preferably, the third solution comprises about 5% sodium atorvastatin.

Preferably, the pH of the third solution is adjusted by the addition of hydrochloric acid, preferably having a concentration of about 15 to 30%, more preferably about 15 to 20%. In preferred embodiments, the pH of the third solution is adjusted to between about 1 and 4.

Preferably, the third organic solvent is a halogen substituted $C_1$ to $C_6$ hydrocarbon, more preferably dichloromethane.

It is preferred that the third organic solvent is added to the third solution at a ratio of about 100 to 200 g third organic solvent for about every 10 g sodium atorvastatin in the third solution.

Preferably, the pH of the organic layer is adjusted by the addition of sodium hydroxide solution, preferably having a concentration of about 20 to 50%. In preferred embodiments, the pH of the organic layer is adjusted to between about 9 and 10.

Preferably, the precipitated amorphous sodium atorvastatin is collected by filtration.

Preferably, the precipitated amorphous sodium atorvastatin is dried, more preferably dried under vacuum.

According to a preferred embodiment, the precipitated amorphous sodium atorvastatin exhibits an X-ray diffraction pattern substantially the same as shown in FIG. 1.

According to another embodiment the precipitated amorphous sodium atorvastatin preferably exhibits an X-ray diffraction pattern comprising peaks expressed in degrees two-theta at approximately 7.87±0.2, 18.18±0.2, 18.87±0.2 and 22.88±0.2.

According to a further embodiment, the precipitated amorphous sodium atorvastatin preferably exhibits an X-ray diffraction pattern comprising peaks expressed in degrees two-theta at approximately 5.45±0.2, 7.87±0.2, 9.52±0.2, 11.02±0.2, 14.2±0.2, 16.4±0.2, 18.18±0.2, 18.87±0.2, 19.76±0.2, 22.88±0.2, 32.27±0.2, 33.35±0.2, 37.86±0.2, 39.99±0.2, 41.13±0.2 and 44.95±0.2.

A further aspect of the present invention relates to amorphous sodium atorvastatin.

According to another aspect of the present invention, there is provided amorphous sodium atorvastatin which exhibits an X-ray diffraction pattern comprising peaks expressed in degrees two-theta at approximately 7.87±0.2, 18.18±0.2, 18.87±0.2 and 22.88±0.2.

According to a further aspect of the present invention, there is provided amorphous sodium atorvastatin which exhibits an X-ray diffraction pattern comprising peaks expressed in degrees two-theta at approximately 5.45±0.2, 7.87±0.2, 9.52±0.2, 11.02±0.2, 14.2±0.2, 16.4±0.2, 18.18±0.2, 18.87±0.2, 19.76±0.2, 22.88±0.2, 32.27±0.2, 33.35±0.2, 37.86±0.2, 39.99±0.2, 41.13±0.2 and 44.95±0.2.

Also provided by the present invention is amorphous sodium atorvastatin which exhibits an X-ray diffraction pattern substantially the same as shown in FIG. 1.

Further provided by the present invention is amorphous sodium atorvastatin produced by any of the methods described herein.

The present invention also relates to crystalline sodium atorvastatin produced by any of the methods described herein.

Preferably, the crystalline sodium atorvastatin has a purity of at least 95%, more preferably at least 98%, further preferably at least 99%.

Preferably, the amorphous sodium atorvastatin has a purity of at least 90%, more preferably at least 93%, further preferably at least 96%, preferably still at least 98%.

Accordingly, the present invention describes a novel crystalline form of sodium atorvastatin, a novel amorphous form of sodium atorvastatin and processes for the preparation thereof.

It is anticipated that both the crystalline form of sodium atorvastatin and the amorphous form of sodium atorvastatin disclosed herein will be useful in the treatment of a variety of diseases which are prevented, ameliorated or eliminated by the administration of a lipid regulating agent. Examples of such diseases include hyperlipemia, primary hyperlipemia, heterozygote familial hyperlipemia, renal hyperlipemia, mixed hyperlipemia, diabetes, atherosclerosis, hypertension, coronary heart disease, cerebral apoplexy and ischemic cerebrovascular disease.

According to another aspect of the present invention, there is, therefore, provided a pharmaceutical composition comprising crystalline sodium atorvastatin or amorphous sodium atorvastatin as described herein.

According to a further aspect of the present invention, there is provided a composition for treating a disease which is prevented, ameliorated or eliminated by the administration of a lipid regulating agent, the composition comprising crystalline sodium atorvastatin or amorphous sodium atorvastatin as described herein.

Preferably, the disease is selected from hyperlipemia, primary hyperlipemia, heterozygote familial hyperlipemia, renal hyperlipemia, mixed hyperlipemia, diabetes, atherosclerosis, hypertension, coronary heart disease, cerebral apoplexy and ischemic cerebrovascular disease.

Also provided by the present invention is a method of treating a disease which is prevented, ameliorated or eliminated by the administration of a lipid regulating agent, the method comprising administering to a patient a therapeutically effective amount of crystalline sodium atorvastatin, amorphous sodium atorvastatin, or a pharmaceutical composition as described herein.

Preferably, the disease is selected from hyperlipemia, primary hyperlipemia, heterozygote familial hyperlipemia, renal hyperlipemia, mixed hyperlipemia, diabetes, atherosclerosis, hypertension, coronary heart disease, cerebral apoplexy and ischemic cerebrovascular disease.

By a therapeutically effective amount, it is meant an amount which is capable of preventing, ameliorating or eliminating the diseases mentioned herein.

The crystalline sodium atorvastatin or amorphous sodium atorvastatin can be mixed with a carrier, diluent or excipient therefor, all of which are well known in the art. For example, suitable carriers may include pills, powders, lozenges, sachets, cachets, elixirs, suspensions, emulsions, solutions, syrups, aerosols, ointments, soft and hard gelatine capsules, suppositories, sterile injectable solutions and sterile packaged powders.

According to a further aspect of the present invention, there is provided a process for preparing the crystalline form of sodium atorvastatin with high purity, the method comprising the following steps:

(a) preparation of amorphous sodium atorvastatin: starting with a sodium atorvastatin solution, adjust the pH to about 1-4 with acid solution, extract with organic solvent, adjust the pH in the organic layer to about 9-10, and collect the precipitate by filtration. Obtain the amorphous sodium atorvastatin after drying under vacuum.

(b) preparation of crystalline sodium atorvastatin: dissolve the obtained amorphous sodium atorvastatin in aqueous alcoholic solvent, add acetone, allow the sodium atorvastatin to crystallize out at low temperature. Collect the crystalline material by filtration and then dry under vacuum.

Preferably, the acid solution used is hydrochloric acid with a concentration ranging from about 15% to 30%. Preferably, the basic solution used is sodium hydroxide solution with a concentration ranging from about 20% to 50%. In preferred embodiments, the organic solvent used is dichloromethane, which is in a mass ratio of about 10-20:1 against the amount of sodium atorvastatin in the solution. The aqueous alcoholic solvent used is preferably ethanol, the amount of ethanol used is preferably in a mass ratio of about 4-10:1 against the amount of sodium atorvastatin in solution. The ketone solvent used is preferably acetone, the amount of acetone used is preferably in a mass ratio of about 5-10:1 against the amount of sodium atorvastatin in solution.

The present invention thus provides a crystalline form of sodium atorvastatin with a high purity. The common practice to prepare calcium atorvastatin usually involves the replacement of sodium with calcium in solution in which the sodium atorvastatin serves only as intermediate without isolation. Therefore, the quality of the isolated calcium salt is not satisfactory in terms of purity. The present invention provides a crystallization process for preparing crystalline sodium atorvastatin with high purity, which can be either used as a pharmaceutical ingredient or converted to calcium atorvastatin with high purity.

An example of the present invention will now be described with reference to the accompanying figures in which:—

FIG. 1 is the powder X-ray diffraction pattern for amorphous sodium atorvastatin; and FIG. 2 is the powder X-ray diffraction pattern for the crystalline sodium atorvastatin of the present invention.

CRYSTALLISATION

EXAMPLE 1

A solution (200 g) containing 10 g of sodium atorvastatin was added to a 500 ml 3-neck flask. The pH was adjusted to 1, dichloromethane (100 g) was added, and then the pH of the organic layer was adjusted to 9 with a 20% sodium hydroxide solution. The precipitate was collected by filtration and then dried under vacuum. Amorphous sodium atorvastatin, designated as Form I, (8.6 g) was thus obtained having an X-ray powder diffraction pattern as shown in FIG. 1.

The amorphous sodium atorvastatin (8.6 g) was dissolved in an 80% ethanol solution (40 g). Acetone (50 g) was then added. The sodium atorvastatin crystallized out on cooling. The crystalline sodium atorvastatin was collected by filtration and dried under vacuum (7.8 g). Highly pure crystalline sodium atorvastatin, designated as Form I, was obtained with an assay purity of 99.3% and a crystal form having an XRD spectrum as shown in FIG. 2.

EXAMPLE 2

A solution (200 g) containing 10 g of sodium atorvastatin was added to a 500 ml 3-neck flask. The pH was adjusted to 1, dichloromethane (100 g) was added, and then the pH of the organic layer was adjusted to 9 with a 20% sodium hydroxide solution. The precipitate was collected by filtration and then dried under vacuum. Amorphous sodium atorvastatin, designated as Form I, (8.6 g) was thus obtained having an X-ray powder diffraction pattern as shown in FIG. 1.

The amorphous sodium atorvastatin (8.6 g) was dissolved in a 98% ethanol solution (100 g). Acetone (100 g) was then added. The sodium atorvastatin crystallized out on cooling. The crystalline sodium atorvastatin was collected by filtration and dried under vacuum (7.8 g). Highly pure crystalline sodium atorvastatin, designated as Form I, was obtained with an assay purity of 99.6% and a crystal form having an XRD spectrum as shown in FIG. 2.

EXAMPLE 3

Hydrochloric acid having a concentration of 15-20% was added to a solution containing sodium atorvastatin and the pH was adjusted to 1-4. Dichloromethane was added to the solution and the organic layer was mixed with 20-50% sodium hydroxide solution until the pH was at 9-10. Generally, the amount of sodium hydroxide used was at a ratio of 10-20 times the amount of sodium atorvastatin used. The precipitate was then collected by filtration and dried under vacuum. Amorphous sodium atorvastatin, designated as Form I, was thus obtained having an XRD spectrum as shown in FIG. 1.

The amorphous sodium atorvastatin was dissolved in an ethanol solution at a ratio of about 4-10 times the amount of sodium atorvastatin used. Acetone was added to the solution at a ration of about 5-10 times the amount of sodium atorvastatin used. Sodium atorvastatin was allowed to crystallize out at a lower temperature, collected by filtration and then dried under vacuum. Highly pure crystalline sodium atorvastatin, designated as Form I, was obtained having an XRD spectrum shown in FIG. 2.

EXAMPLE 4

A solution (200 g) containing 10 g of sodium atorvastatin was added to a 500 ml 3-neck flask. The pH was adjusted to 1, dichloromethane (100 g) was added, and then the pH of the organic layer was adjusted to 9 with a 20% sodium hydroxide solution. The precipitate was collected by filtration and then dried under vacuum. Amorphous sodium atorvastatin, designated as Form I, (8.6 g) was thus obtained having an X-ray powder diffraction pattern as shown in FIG. 1.

The amorphous sodium atorvastatin (8.6 g) was dissolved in a 95% ethanol solution (100 g). Acetone (100 g) was then added. The sodium atorvastatin crystallized out on cooling. The crystalline sodium atorvastatin was collected by filtration and dried under vacuum (7.2 g). Highly pure crystalline sodium atorvastatin, designated as Form I, was obtained with an assay purity of 99.6% and a crystal form having an XRD spectrum as shown in FIG. 2.

The sodium atorvastatin salt produced by the above methods had the following structure:—

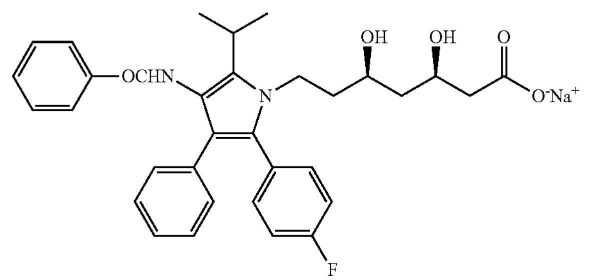

atorvastatin sodium salt I

TABLE 1

The XRD spectrum for the amorphous form obtained according to the examples above.

| 2 theta (degree) | d (A) | $I/I_0$ | I.cps | FWHM |
|---|---|---|---|---|
| 5.451 | 16.1985 | 10.3 | 291 | |
| 7.865 | 11.2313 | 74.7 | 2107 | |
| 9.516 | 9.2868 | 5.1 | 145 | |
| 11.018 | 8.0237 | 9.5 | 269 | |
| 14.201 | 6.2317 | 14.6 | 413 | |
| 16.399 | 5.4009 | 29.4 | 829 | 0.20 |
| 18.179 | 4.8758 | 100 | 2820 | |
| 18.873 | 4.6982 | 67.2 | 1894 | |
| 19.761 | 4.4890 | 29.1 | 821 | |
| 22.875 | 3.8844 | 87.5 | 2468 | 0.36 |
| 32.271 | 2.7717 | 12.9 | 363 | |
| 33.354 | 2.6842 | 7.0 | 197 | |
| 37.860 | 2.3744 | 16.4 | 462 | |
| 39.994 | 2.2525 | 6.2 | 176 | |
| 41.129 | 2.1929 | 5.0 | 140 | |
| 44.947 | 2.0151 | 6.3 | 179 | |

Peak Number: 16
Highest Peak: 2820
Total Diffraction Intensity: 3453641
Total Purity Intensity: 798951
Total Purity Intensity/Total Diffraction Intensity: 0.231

TABLE 2

The XRD spectrum for the crystalline form obtained according to the examples above.

| 2 theta (degree) | d (A) | $I/I_0$ | I.cps | FWHM |
|---|---|---|---|---|
| 3.360 | 26.2763 | 55.3 | 2186 | |
| 4.801 | 18.3920 | 23.5 | 927 | 0.25 |
| 5.593 | 15.7871 | 11.5 | 455 | 0.25 |
| 7.405 | 11.9290 | 45.8 | 1811 | 0.25 |
| 8.297 | 10.6482 | 73.7 | 2910 | 0.28 |
| 8.812 | 10.0272 | 93.1 | 3676 | 0.31 |
| 9.686 | 9.1241 | 100 | 3950 | 0.31 |
| 10.235 | 8.6354 | 22.7 | 897 | |
| 11.127 | 7.9451 | 18.4 | 727 | 0.22 |
| 11.209 | 7.8875 | 44.7 | 1764 | 0.42 |
| 12.217 | 7.2386 | 24.2 | 955 | 0.28 |
| 12.799 | 6.9109 | 17.6 | 695 | 0.25 |
| 13.851 | 6.3880 | 15.4 | 607 | 0.36 |
| 15.990 | 5.5381 | 26.1 | 1030 | 0.48 |
| 16.399 | 5.4010 | 21.0 | 828 | 0.20 |
| 16.952 | 5.2260 | 34.0 | 1344 | 0.42 |
| 17.818 | 4.9739 | 17.6 | 696 | 0.25 |
| 18.151 | 4.8834 | 40.0 | 1580 | 0.28 |
| 18.462 | 4.8017 | 30.9 | 1222 | 0.28 |
| 19.481 | 4.5530 | 69.2 | 2735 | 0.48 |
| 20.860 | 4.2549 | 58.3 | 2302 | 0.45 |
| 21.818 | 4.0702 | 31.7 | 1252 | 0.36 |
| 22.875 | 3.8845 | 62.5 | 2469 | 0.36 |
| 23.977 | 3.7083 | 17.3 | 683 | 0.39 |
| 28.339 | 3.1467 | 9.0 | 356 | 0.25 |
| 32.271 | 2.7716 | 9.2 | 365 | |
| 33.401 | 2.6804 | 7.8 | 308 | 0.25 |

Peak Number: 27
Highest Peak: 3950
Total Diffraction Intensity: 3453641
Total Purity Intensity: 798951
Total Purity Intensity/Total Diffraction Intensity: 0.231

The invention claimed is:

1. A pharmaceutical composition comprising crystalline sodium atorvastatin, wherein said crystalline sodium atorvastatin is prepared by a method comprising:

(a) adding amorphous sodium atorvastatin to a first organic solvent to form a first solution;

(b) adding a second organic solvent to the first solution to form a second solution;

(c) allowing sodium atorvastatin to crystallize out from the solution; and (d) collecting the crystallized sodium atorvastatin, wherein the first organic solvent is ethanol and the second organic solvent is acetone, thereby obtaining crystalline sodium atorvastatin which exhibits an X-ray powder diffraction pattern comprising peaks expressed in degrees two-theta at approximately 3.36±0.2, 4.8±0.2, 5.59±0.2, 7.41±0.2, 8.3±0.2, 8.81±0.2, 9.69±0.2, 10.24±0.2, 11.13±0.2, 11.21±0.2, 12.22±0.2, 12.8 ±0.2, 13.85±0.2, 15.99±0.2, 16.40±0.2, 16.95±0.2, 17.82±0.2, 18.15±0.2, 18.46±0.2, 19.48±0.2, 20.86±0.2, 21.82±0.2, 22.88±0.2, 23.98±0.2, 28.34±0.2, 32.27±0.2, and 33.40±0.2.

2. The pharmaceutical composition of claim 1, wherein the amorphous sodium atorvastatin is added to the first organic solvent at a ratio of about 8 to 10 g amorphous atorvastatin for about every 40 g to 100 g first organic solvent.

3. The pharmaceutical composition of claim 1, wherein the second organic solvent is added to the first solution at a ratio of about 50 to 100 g second organic solvent for about every 8 to 10 g amorphous atorvastatin used in (a).

4. The pharmaceutical composition of claim 1, wherein the first organic solvent comprises at least about 75% organic solvent in solution.

5. The pharmaceutical composition of claim 1, wherein the crystallized sodium atorvastatin is collected by filtration.

6. The pharmaceutical composition of claim 1, wherein the collected crystallized sodium atorvastatin is dried.

7. The pharmaceutical composition of claim 6, wherein the collected crystallized sodium atorvastatin is dried under vacuum.

8. The pharmaceutical composition of claim 1, further comprising the following for the preparation of amorphous sodium atorvastatin for use in (a):

(i) preparing a third solution comprising sodium atorvastatin;

(ii) adjusting the pH of the third solution to an acid pH;

(iii) adding a third organic solvent to form a fourth solution;

(iv) isolating an organic layer;

(v) adjusting the pH of the organic layer to an alkali pH; and (vi) collecting precipitated amorphous sodium atorvastatin wherein the third organic solvent is dichloromethane.

9. The pharmaceutical composition of claim 8, wherein the third solution comprises about 5% sodium atorvastatin.

10. The pharmaceutical composition of claim 8, wherein the pH of the third solution is adjusted by the addition of hydrochloric acid.

11. The pharmaceutical composition of claim 10, wherein the hydrochloric acid has a concentration of about 15 to about 20%.

12. The pharmaceutical composition of claim 8, wherein the pH of the third solution is adjusted to between about 1 and about 4.

13. The pharmaceutical composition of claim 8, wherein the third organic solvent is added to the third solution at a ratio of about 100 to 200 g third organic solvent for about every 10 g sodium atorvastatin in the third solution.

14. The pharmaceutical composition of claim 8, wherein the pH of the organic layer is adjusted by the addition of sodium hydroxide solution.

15. The pharmaceutical composition of claim 14, wherein the sodium hydroxide solution has a concentration of about 20 to about 50%.

16. The pharmaceutical composition of claim 8, wherein the pH of the organic layer is adjusted to between about 9 and about 10.

17. The pharmaceutical composition of claim 8, wherein the precipitated amorphous sodium atorvastatin is collected by filtration.

18. The pharmaceutical composition of claim 8, wherein the precipitated amorphous sodium atorvastatin is dried.

19. The pharmaceutical composition of claim 18, wherein the precipitated amorphous sodium atorvastatin is dried under vacuum.

20. The pharmaceutical composition of claim 1 wherein the crystalline sodium atorvastatin has a purity of at least 99%.

21. The pharmaceutical composition of claim 1 wherein the crystalline sodium atorvastatin is mixed with a carrier.

22. The pharmaceutical composition of claim 21 wherein the carrier is selected from the group consisting of pills, powders, lozenges, sachets, cachets, elixirs, suspensions, emulsions, solutions, syrups, aerosols, ointments, soft gelatin capsules, hard gelatin capsules, suppositories, sterile injectable solutions and sterile packaged powders.

* * * * *